United States Patent [19]

Sampathkumar et al.

[11] 4,394,308

[45] Jul. 19, 1983

[54] METHOD OF PRODUCING α-L-ASPARTYL-L-PHENYLALANINE METHYLESTERS

[75] Inventors: Prathivadibhayankaram S. Sampathkumar, Parsippany; Basant K. Dwivedi, Randolph, both of N.J.

[73] Assignee: Chimicasa GmbH, Switzerland

[21] Appl. No.: 305,693

[22] Filed: Sep. 25, 1981

Related U.S. Application Data

[63] Continuation of Ser. No. 150,881, May 27, 1980, abandoned.

[51] Int. Cl.$^3$ ............................................. C07C 103/52
[52] U.S. Cl. ............................................. 260/112.5 R
[58] Field of Search ............................... 260/112.5 R

[56] References Cited

U.S. PATENT DOCUMENTS 3,492,131  1/1970  Schlatter .................. 260/112.5 R
3,972,860  8/1976  Moriarty et al. ........... 260/112.5 R

*Primary Examiner*—Delbert R. Phillips
*Attorney, Agent, or Firm*—Richard P. Crowley

[57] ABSTRACT

A method for the preparation of α-L-aspartyl-L-phenylalanine methylester, which method comprises reacting an ester of L-phenylalanine with N and α-carboxyl-protected L-aspartic acid, to produce an α-L-aspartyl-L-phenylalanine methylester without racemization and isomer formation and in high yields.

4 Claims, No Drawings

METHOD OF PRODUCING α-L-ASPARTYL-L-PHENYLALANINE METHYLESTERS

This is a continuation of application Ser. No. 150,881, filed May 27, 1980, now abandoned.

BACKGROUND OF THE INVENTION

The discovery of the sweetness of the dipeptide α-L-aspartyl-L-phenylalanine methylester was reported in 1969 by R. H. Mazur et al (*Jour. Amer. Chem. Soc.*, 91, 2684, 1969). Since then, several methods have been developed for preparing the compound (see, for example, U.S. Pat. Nos. 3,475,403; 3,833,553; 3,798,206; 3,769,333; and 3,933,781).

In U.S. Pat. No. 3,475,403, Mazur et al react N-benzyloxycarbonyl-L-aspartic acid α-p-nitrophenol and β-benzylester and L-tyrosine methylester, to produce the β-benzyl-N-benzyloxycarbonyl-L-aspartyl-L-tyrosine methylester. In U.S. Pat. No. 3,933,781, L-phenylalanine and N-formyl-L-aspartic anhydride are used to form N-formyl-α-L-aspartyl-L-phenylalanine which is deformylated and then esterified to obtain the methylester compound.

SUMMARY OF THE INVENTION

The present invention relates to an improved method for the preparation of the sweetener α-L-aspartyl-L-phenylalanine methylester.

It has been found that α-L-aspartyl-L-phenylalanine alkylesters, particularly the methylester sweetener compound, may be produced in high yields; for example, over 70%, and without racemization and isomer formation of the nonsweetener isomeric compound.

The improved method provides for an esterification reaction between L-aspartic acid and an alcohol, such as benzyl alcohol, to provide an esterified L-aspartate having a free α-carboxyl group, followed by a reaction of the hydrogen on the free amino group of the esterified L-aspartate with a carbobenzoxy halide, such as the chloride, to produce N-carbobenzoxy-β-benzyl-L-aspartate. This compound has the α-carboxyl group of the aspartic acid free for coupling with any desired carboxyl-protected amino acid.

Thus, an alkylester, such as the methylester, of L-phenylalanine may then be coupled by a reaction with the free amino group of the L-phenylalanine methylester with the free α-carboxyl group of the N-carbobenzoxy-β-benzyl-L-aspartate, to provide the coupled aspartate-phenylalanine compound. This coupled compound is then hydrogenated; for example, by hydrogen in the presence of a catalyst or by other methods, to reintroduce the free amino group and one of the free carboxyl groups of the L-aspartate portion of the molecule, resulting in the sweetener compound α-L-aspartyl-L-phenylalanine methyl ester.

The improved method avoids the difficulties associated with prior-art methods, wherein the carboxyl group of the L-phenylalanine has been protected, and the free amino group is coupled with the L-aspartic acid. This technique produced low yields, since two isomers were formed, only in one of which the alpha-carboxyl resulted in the desired sweetener compound. The improved method provides protection through the use of a carboxyl-protecting group for the L-aspartic acid and through the use of an amino-protective group for the free amino group of the L-aspartic acid.

The resulting aspartate compound, with the amino group and the β-carboxyl group protected, then may be coupled with the alkylester, L-phenylalanine. The resulting coupled reaction product is then hydrogenated, to remove the amino and β-carboxyl-protecting groups from the aspartate portion of the molecule, to provide the sweetener α-L-aspartyl-L-phenylalanine in high yield. Thus, the improved method blocks the β-free-carboxyl group and then the free amino group of the aspartic acid, then couples the resulting α-carboxyl-free acid of the aspartate with a free amino group of a carboxyl-blocked phenylalanine, and subsequently hydrogenates or otherwise frees the β-carboxyl group and the amino group of the aspartate, to produce the α-L-aspartyl-L-phenylalanine.

The improved method is set forth in a general schematic sequence as follows:

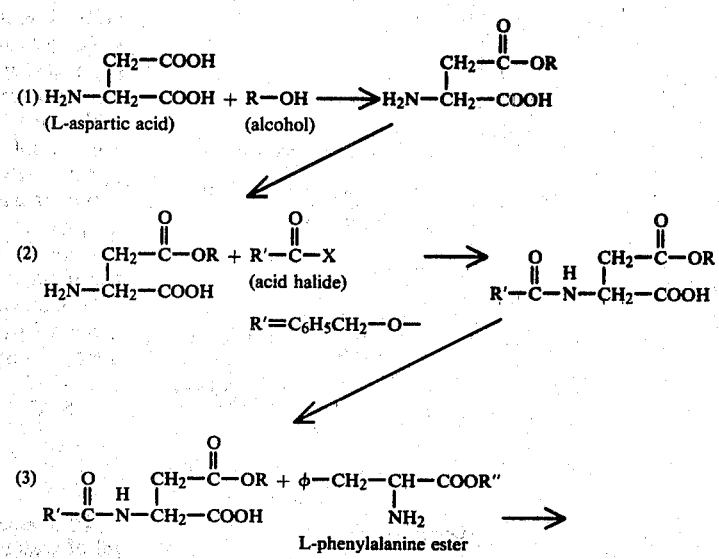

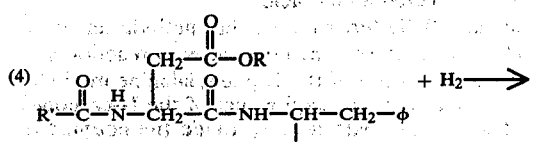

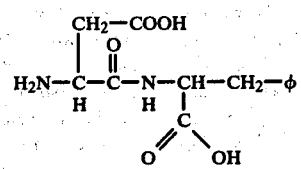

α-L-aspartyl-L-phenylalanine wherein ROH is an alcohol; for example, an aliphatic or benzyl alcohol;

$$R'-\overset{O}{\overset{\|}{C}}-X$$

is an oxy acid halide, with X; for example, chloride, and R' a benzyl oxy or aliphatic group; and R'' is an alkyl; for example, $C_1-C_4$ alkyl; for example, methyl.

Various amino and carboxyl blocking groups may be selected and should protect the sites from reaction, and yet be removed easily, such as by hydrogenation, to reform the free amino group and the free β-carboxyl group of the aspartate, after the coupling between the blocked aspartate and the blocked phenylalanine.

The preferred reaction procedure is shown as follows:

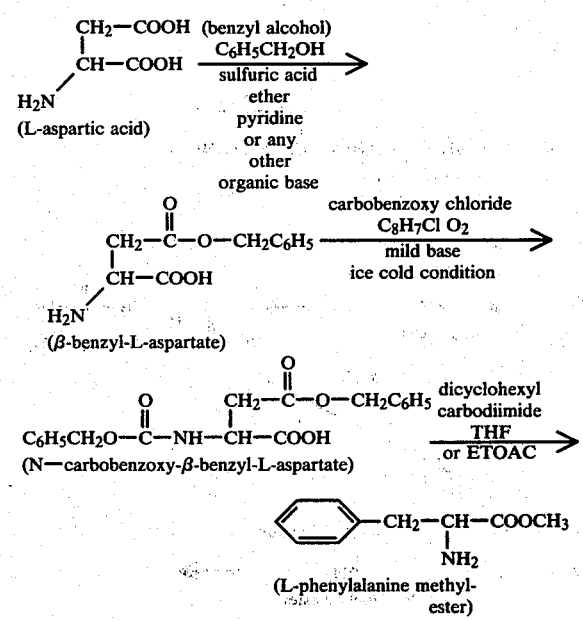

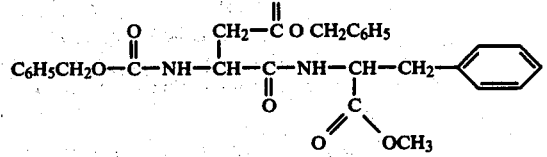

(β-benzyl-N—carbobenzoxy-L-aspartyl-L-phenylalanine methylester)

$H_2/Pd$
atmospheric pressure
methanol containing
few drops of AcOH

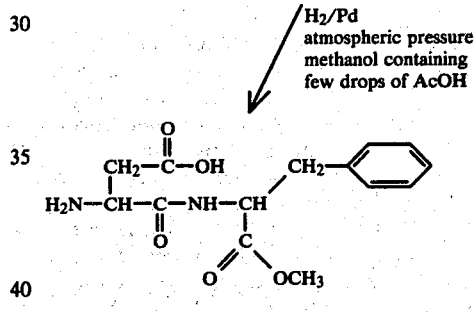

α-L-aspartyl-L-phenylalanine methylester

EXAMPLE 1

β-benzyl-L-aspartate

Sulfuric acid (15 ml) was added to anhydrous ether (150 ml) and benzyl alcohol (150 ml) in a one-liter flask. Ether was removed under vacuum and L-aspartic acid (26.8 gm) was added in several portions while mixing with a magnetic stirrer. A clear solution was obtained which was left at 25° C. for 12–16 hours. 300 ml of 95% ethyl alcohol were then added, followed by 75 ml of pyridine. Pyridine or any organic base, such as triethylamine or triethanolamine, should be added slowly (one drop per minute), with vigorous stirring of the contents. The mixture was cooled overnight and the solid material formed was washed several times with ether. The solid material was recrystallized from water (with a few drops of pyridine), to yield 31 gms (70% yield) of β-benzyl-L-aspartate, with a reported melting point of 218° C.-21° C. and an observed melting point of 223° C.-25° C.

EXAMPLE 2

N-carbobenzoxy β-benzyl-L-aspartate

To a solution of 40 gms of sodium bicarbonate in 400 ml of water in a one-liter beaker was added 22.3 gms of the β-benzyl-L-aspartate of Example 1, and the mixture was stirred vigorously with a magnetic stirrer. A cloudy solution was obtained, to which was added 15 ml of 1 N sodium hydroxide. Stronger alkali tends to debenzylate the β-carboxyl, and, if no solution is obtained at this stage, it will result in a mixture of products. To the reaction mixture was added 17 gms of carbobenzoxy chloride (benzyl chloroformate) in about five portions over a period of 45 minutes. Stirring was continued for another 1 hour, and unreacted carbobenzoxy chloride was removed by extracting with ether (100 ml×2). The aqueous layer was acidified to pH 5 with 6 N hydrochloric acid, with cooling and stirring. A white crystalline solid was separated. It was filtered, dried and recrystallized from benzene-ethylacetate, to provide 29.5 gms (yield—80%), with an observed melting point of 106° C. to 108° C.

For comparison, the compound β-benzyl-N-carbobenzoxy-L-aspartate was prepared by another route (see A. Berger and E. Katchalski, *Jour. Amer. Chem. Soc.*, 73, p. 4084–1951). A mixture of 2 N sodium hydroxide (10 ml) water (48 ml) and dioxane (120 ml) was added to a solution of dibenzyl-N-carbobenzoxy-L-aspartate (9.12 g) in dioxane (75 ml) and water (40 ml). A single layer was formed. The contents were left at room temperature for 24 hours and the pH adjusted to 5.5 with hydrochloric acid. The solvents were evaporated in vacuo. The residue was treated with 1 N potassium bicarbonate (20 ml), and the mixture was extracted with ether to remove the unreacted dibenzyl ester. The aqueous layer was acidified with 6 N hydrochloric acid and then β-benzyl-N-carbobenzoxy-L-aspartate separated out as white crystals (4.6 gms). It was recrystallized from benzene, with a melting point of 107° C. to 108° C. The compound obtained by this method and the one prepared above were identical as regards melting point, infrared and thin-layer chromatography.

EXAMPLE 3

β-benzyl-N-carbobenzoxy-L-aspartyl-L-phenylalanine 7.2 gms of β-benzyl-N-carbobenzoxy-L-aspartate were dissolved in 250 ml of tetrahydrofuran (THF), and to this solution was added 4.30 gms of L-phenylalanine methylester in 25 ml ethylacetate (ETOAC). The coupling reaction was done in the presence of dicyclohexylcarbodiimide (4.12 gms in 25 ml tetrahydrofuran) and stirred for 2 hours. The dicyclohexylurea (DCU) formed was filtered off and the residue, after several washings with methanol, was stripped off of all DCU and crystallized from 2-propanol, to give 9.3 gms of the desired coupled compound of β-benzyl-N-carbobenzoxy-L-aspartyl-L-phenylalnine (yield—90%), with a reported melting point of 119° C.-20° C. and an observed melting point of 118° C.-20° C.

EXAMPLE 4

α-L-aspartyl-L-phenylalanine methylester

Hydrogenation of the coupled β-benzyl-N-carbobenzoxy-L-aspartyl-L-phenylalanine methylester was carried out by dissolving 5.19 gms of β-benzyl-N-carbobenzoxy-L-aspartyl-L-phenylalanine methylester in 250 ml of methanol containing 5 ml of glacial acetic acid (AcOH). To this mixture was added 1.5 gms of palladium/charcoal and a slow stream of hydrogen passed at atmospheric pressure and room temperature. The reaction was complete in 3 hours. After filtering and evaporating the solvents, the residue was crystallized from 95% alcohol (yield—90%), with an observed melting point of 244° C. to 246° C. (d) and a reported melting point of 248° C. to 249° C. (d). The sample was found to be identical in all respects (IR, TLC, m.pt and m.mpt) with a commercial sample of the compound.

What we claim is:
1. A method of preparing α-L-aspartyl-L-phenylalanine alkylester in high yield without substantial isomer formation of the alkylester, which method comprises:
  (a) reacting L-aspartic acid with an alcohol, to provide an esterified aspartate compound with the beta-carboxyl group blocked by the ester group, and having a free alpha-carboxyl group;
  (b) reacting the amino group of the esterified aspartate compound with a carbobenzoxy halide, to provide an N-carbobenzoxyl, esterified, L-aspartate compound with a free alpha-carboxyl group;
  (c) reacting the N-carbobenzoxyl, esterified, aspartate compound in a coupling reaction with an alkylester of L-phenylalanine, by reaction of the free amino group of the L-phenylalanine with the free alpha-carboxyl group of the aspartate compound, to provide a coupled aspartate-phenylalanine compound;
  (d) hydrogenating the coupled compound, to reintroduce into the molecule the free amino group and one of the free carboxyl groups of the aspartate portion of the coupled compound; and
  (e) recovering the L-aspartyl-L-phenylalanine alkylester in a high yield, without substantial racemization of the α-L-aspartyl-L-phenylalanine alkylester.

2. The method of claim 1 wherein the alkylester of L-phenylalanine is the methylester.

3. The method of claim 1 wherein the alcohol comprises benzyl alcohol.

4. The method of claim 1 wherein the carbobenzoxy halide comprises carbobenzoxy chloride.

* * * * *